United States Patent [19]

Boltralik

[11] Patent Number: 5,223,493
[45] Date of Patent: Jun. 29, 1993

[54] ANTI-INFLAMMATORY COMPOUNDS FOR OPHTHALMIC USE

[75] Inventor: John J. Boltralik, Ft. Worth, Tex.

[73] Assignee: Alcon Laboratories, Inc., Fort Worth, Tex.

[21] Appl. No.: 852,889

[22] Filed: Mar. 17, 1992

Related U.S. Application Data

[63] Continuation of Ser. No. 613,595, Nov. 13, 1990, abandoned, which is a continuation-in-part of Ser. No. 299,997, Jan. 23, 1989, abandoned, which is a continuation of Ser. No. 922,810, Oct. 23, 1986, abandoned, which is a continuation of Ser. No. 687,278, Dec. 28, 1984, abandoned.

[51] Int. Cl.$^5$ .............................................. A61K 31/56
[52] U.S. Cl. .................................... 514/180; 514/912
[58] Field of Search .......................... 514/180, 181, 912

[56] References Cited

U.S. PATENT DOCUMENTS 4,588,530 5/1986 Lee ................................... 260/397.45
4,617,299 10/1986 Knepper ............................... 514/178

FOREIGN PATENT DOCUMENTS 936526 11/1973 Canada .................................... 260/60

OTHER PUBLICATIONS

Philips, et al., *The Lancet*, 767–768 (Apr. 7, 1984).
Knepper, *Esp. Eye Res.*, 27:567 (1978).
Southren, et al., *Invest. Ophthal. Vis. Sci.*, 26:393 (1985).
Southren et al., *Invest. Ophthal. Vis. Sci.*, 28:901 (1987).
Boltralik et al., *Invest. Ophthal.*, 13 (Supp.):78 (1974).

*Primary Examiner*—Frederick E. Waddell
*Assistant Examiner*—Zohreh A. Fay
*Attorney, Agent, or Firm*—Julie J. L. Cheng; Gregg C. Brown; James A. Arno

[57] ABSTRACT

Anti-inflammatory compounds, a method of treating inflamed ocular tissue and compositions of these compounds are described. The compounds are derivatives and analogues of known steroid compounds (e.g., dexamethasone) and are advantageously characterized in that they do not cause any significant increase in intraocular pressure during chronic use.

16 Claims, No Drawings

ANTI-INFLAMMATORY COMPOUNDS FOR OPHTHALMIC USE

This application is a continuation of application Ser. No. 07/613,595, filed Nov. 13, 1990, now abandoned, which is a continuation-in-part of application Ser. No. 07/299,997 filed Jan. 23, 1989, now abandoned, which is a continuation of application Ser. No. 06/922,810 filed Oct. 23, 1986, now abandoned, which is a continuation of application Ser. No. 06/687,279 filed Dec. 28, 1984, now abandoned.

BACKGROUND OF THE INVENTION

1. Field of the Invention

The present invention relates to novel derivatives of known anti-inflammatory steroids, processes useful for their preparation, and use of a these novel derivatives in the treatment of ophthalmic inflammatory disorders. More particularly, this invention relates to the treatment of ophthalmic inflammatory disorders with novel derivatives of known anti-inflammatory steroids, wherein the novel derivatives do not cause any significant increase in intraocular pressure.

2. Discussion of Related Art

Anti-inflammatory steroids, such as hydrocortisone, prednisolone, dexamethasone, and fluorometholone, are very useful in controlling a wide range of ophthalmic inflammatory conditions. This usefulness may be somewhat negated due to a steroid-induced side effect associated with the chronic use of these compounds. This side effect may be manifested by a rise in intraocular pressure (IOP) in steroid-sensitive patients (steroid-responders), an increase in IOP in glaucoma sensitive patients, or an exacerbation of IOP in patients suffering from frank primary open angle glaucoma. Further discussion of this side effect is presented in an article by Phillips, et al., *The Lancet*, 767–768 (Apr. 7, 1984).

The above-described manifestations can generally be tolerated in most patients over a relatively short treatment period (i.e., four to six weeks, or less); however, the increase in IOP caused by these compounds is generally unacceptable over extended periods of treatment (i.e., one to twelve months, or more), especially in individuals subject to chronic eye inflammation. The increased intraocular pressure associated with the short term use of these s compounds may also be unacceptable in certain patients, such as patients already suffering from an elevated IOP (e.g., glaucoma patients). A need therefore exists for an effective means of treating inflamed ocular tissue without risk of elevating IOP. The present invention is directed to satisfying this need.

SUMMARY OF THE INVENTION

The present invention is directed to novel steroidal C21 ether derivatives, ophthalmic pharmaceutical compositions containing the derivatives, and methods of treating ophthalmic inflammatory disorders with these compositions wherein no significant increase in intraocular pressure results.

It is accepted, from studies of structure-activity relationships in steroid chemistry, that seemingly minor structural modifications in a steroid molecule can either significantly enhance or adversely affect the pharmacological properties of the compound being studied, presumably by altering the action of the drug at the target cells. These modifications may confer agonistic or antagonistic properties to the steroid molecule. Agonistic drugs are broadly defined as compounds which elicit or activate a biochemical response in situations where the mechanism which elicits the response is undefined. On the other hand, antagonistic drugs are broadly defined as inhibitors of the above-identified selective responses. For example, it has been established that certain side chain modifications affect IOP regulation by depressing or inhibiting the systems responsible for directing the synthesis of proteins which regulate the unwanted IOP side effects. Therefore, if a given steroid is designed to have properties which provide both characteristics of agonism with respect to the retention of anti-inflammatory properties, and antagonism with respect to complete suppression of IOP increase, a true separation of effects is achieved.

The present invention is based on the discovery of novel derivatives of certain known anti-inflammatory steroids, such as dexamethasone and fluocinolone, which confer the desired separation of effects. For example, replacement of the proton of the dexamethasone C21 hydroxyl group with a methyl group to produce a C21 methyl ether results in a compound having the anti-inflammatory properties of dexamethasone, but without elevation of intraocular pressure, contrary to what is normally seen with dexamethasone and other steroids. This holds true even with chronic use (e.g., one month or longer).

DETAILED DESCRIPTION OF THE INVENTION

The steroid derivatives which have been found to exhibit the above-discussed separation of effects have the following formulae:

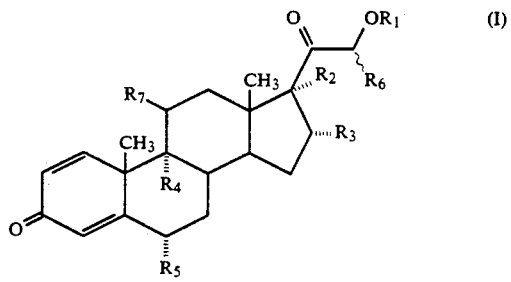

wherein:

$R_1$ is selected from substituted or unsubstituted: $C_1$–$C_5$ alkyl; $C_3$–$C_6$ (ring) and $C_1$–$C_3$ (alkyl) cycloalkyl and cycloalkylalkyl; aryl and arylalkyl, such as phenyl and benzyl; and $C_2$–$C_5$ alkenyl and alkynyl; wherein the substituent or substituents are selected from $C_1$–$C_6$ alkyoxy and alkyl; $C_2$–$C_6$ alkoxyalkyl, alkoxyalkoxyalkyl, alkylthioalkyl, hydroxyalkyl, aminoalkyl, nitriloalkyl; $C_4$–$C_8$ (beta-carboxyalkoxy)alkyl; and $C_2$–$C_6$ alkenoxy and alkynoxy;

$R_2$ is selected from substituted or unsubstituted: alkyl, alkenyl and alkynyl; acyl (—COOR'; wherein, for example, R' is a $C_1$–$C_6$ alkyl); and hydroxyl; wherein the substituent or substituents are selected from: $C_1$–$C_3$ alkyl; hydroxyl; and halogen (F,Cl, and Br);

$R_3$ is selected from methyl and hydroxyl;

$R_4$ is selected from hydrogen, fluoro, and chloro;

$R_5$ is selected from hydrogen, methyl, fluoro, and chloro;

$R_6$ is selected from hydrogen, methyl, ethyl, and allyl; and $R_7$ is selected from hydroxyl, acetate, propionate, and butyrate; and:

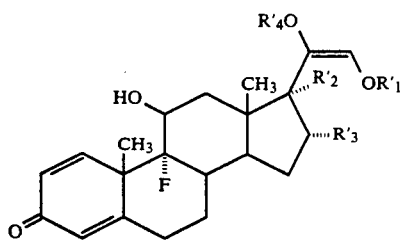

wherein:

$R'$ is selected from substituted or unsubstituted: $C_1$-$C_5$ alkyl, alkenyl, and alkynyl;

$R'_2$ is selected from substituted or unsubstituted: hydrogen; $C_1$-$C_6$ alkyl, alkenyl, alkynyl; acyl; and hydroxyl; wherein the substituent or substituents are selected from: $C_1$-$C_3$ alkyl; hydroxyl; and halogen;

$R'_3$ is selected from methyl and hydroxyl; and $R'_4$ is selected from $C_1$-$C_5$ alkyl, alkenyl, and alkynyl.

These compounds possess anti-inflammatory activity similar to that of known steroids (e.g., dexamethasone), but do not significantly elevate intraocular pressure when applied to inflamed ocular tissue.

The preferred compounds of Formula (I) are those in which $R_1$, $R_2$, $R_3$, $R_4$, $R_5$, $R_6$, and $R_7$ are as follows:

$R_1$ is selected from methyl, ethyl, propyl, butyl, allyl, cyclopropyl, cyclobutyl, cyclopentyl, cyclohexyl, phenyl, benzyl, isopropyl, isobutyl, isoamyl, isovaleryl, 2-propynyl, 2-methoxymethyl, methylthiomethyl, hydroxyethyl, and methoxyethylmethyl;

$R_2$ is selected from methyl, ethyl, propyl, butyl, amyl, acetate, propionate, butyrate, valerylate, 2-propynyl and a hydroxyl;

$R_3$ is selected from methyl and hydroxyl;

$R_4$ is selected from hydrogen, fluoro, and chloro;

$R_5$ is selected from hydrogen, methyl, fluoro, and chloro;

$R_6$ is selected from hydrogen, methyl, ethyl, and allyl; and $R_7$ is selected from hydroxyl, acetate, and propionate.

The preferred compounds of Formula (II) are those in which $R'_1$, $R'_2$, $R'_3$, and $R'_4$ are as follows:

$R'_1$ is selected from methyl, ethyl, and allyl;

$R'_2$ is selected from hydroxyl, acetate, and propionate;

$R'_3$ is selected from methyl and hydroxyl; and $R'_4$ is selected from methyl, ethyl, and allyl.

The preferred subclasses of compounds within these preferred classes of compounds are as follows:

Subclass compounds of Formula (I) wherein $R_2$, $R_3$, and $R_4$ are, respectively, hydroxyl, methyl, and fluoro; especially preferred are compounds of Examples 1-6 and 8-13 shown below;

Subclass 2: compounds of Formula (I) wherein $R_5$ is methyl; compounds of Subclass 1 are especially preferred;

Subclass 3: compounds of Formula (I) wherein $R_3$, $R_4$, and $R_5$ are, respectively, methyl, fluoro, and hydrogen; especially preferred are compounds of Examples 1-6 and 8-14 shown below;

Subclass 4: compounds of Formula (I) wherein $R_2$ and $R_3$ are hydroxyl and $R_4$ and $R_5$ are fluoro;

Subclass 5: compounds of Formula (I) wherein $R_2$ is selected from hydrogen and carboalkyl, such as, acetate, propionate, butyrate, valerylate, and 2-propynyl; compounds in which $R_3$ is hydroxyl and $R_4$ and $R_5$ are fluoro are especially preferred; and Subclass 6: compounds of Formula (II) wherein $R'_1$ is selected from methyl, ethyl, and allyl; $R'_2$ is selected from hydroxyl, acetate, and propionate; and $R'_3$ is methyl.

The following species are particularly preferred. The compound identified as number 7 is an especially preferred species of Subclass 6. The compounds are numbered in correspondence with the examples which follow the structures.

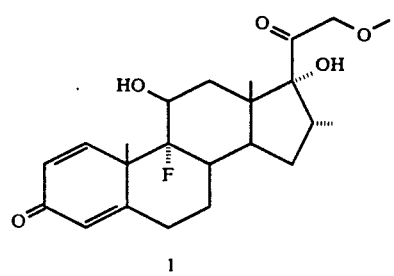

1

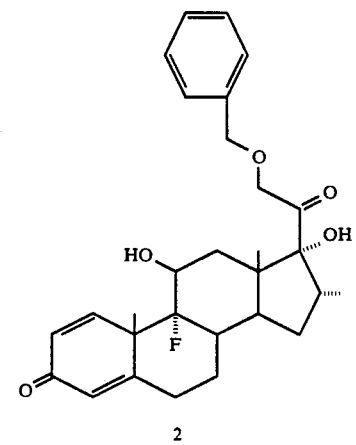

2

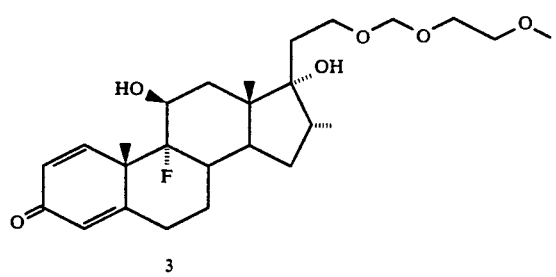

3

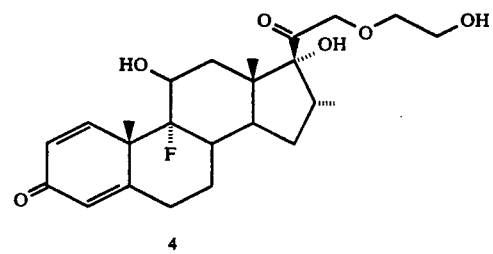

4

-continued

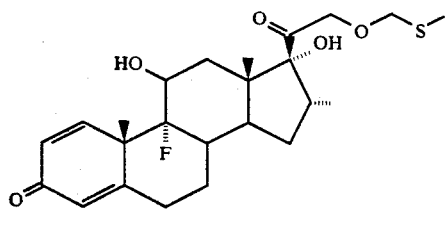
5

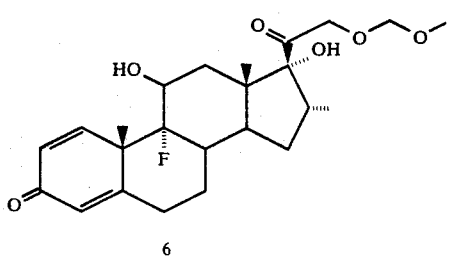
6

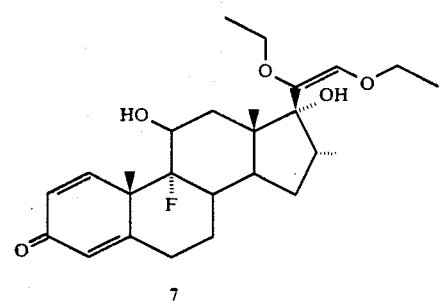
7

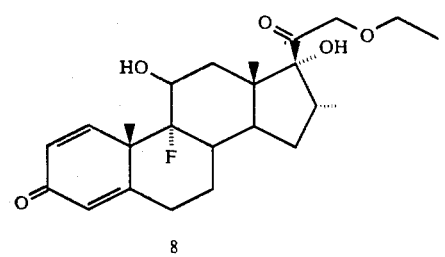
8

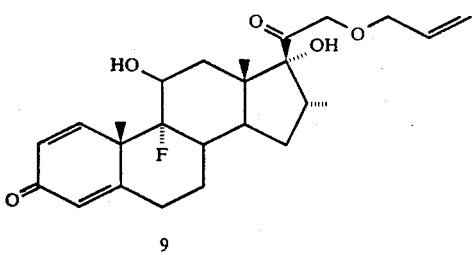
9

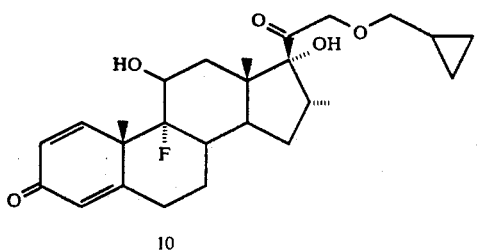
10

-continued

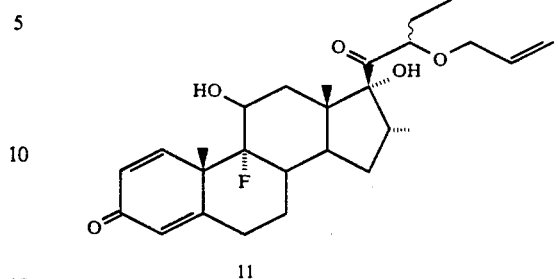
11

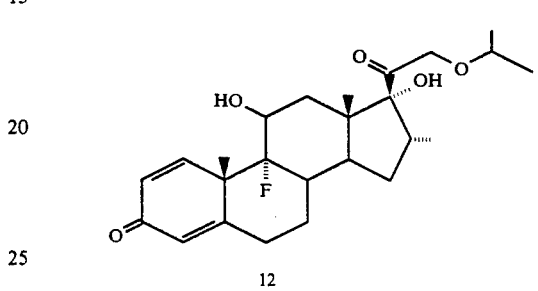
12

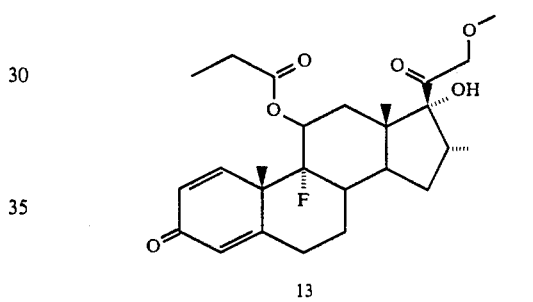
13

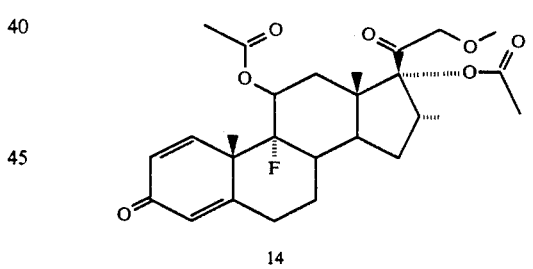
14

The above-described compounds are prepared from known starting materials using the Williamson ether synthesis or modifications thereof, such as: phase transfer catalysis; use of solid bases such as KOH, NaOH, or K₂CO₃, metal hydrides such as NaH, or organic bases such as N,N-diisopropylethylamine, tetramethylguanidine, or 1,8-diazabicyclo[5.4.0]-undec-7-ene in the presence of non-activated or activated halogenated alkylating reagents respectively under anhydrous conditions using aprotic solvents having high dielectric constants. This is further extended to the use of the steroid substrates as the electrophile, rather than as the nucleophile, such as is the a case with tosylates, mesylates, or halides in syntheses of "S" or "O" ethers, or the preparation of ethers from metal catalyzed azide carbene/alcohols or, similarly, using the same reagents via fluoroboric or boron trifluoride etherate catalysis. Monoethers of the C21 methylene hydroxy group are preferred and are secondary to "C" and "O" bialkylation at C21 and/or "O" s bialkylation at C20, C21.

The above-described dexamethasone ether derivatives of the present invention may be synthesized by means of liquid-liquid or liquid-solid phase transfer catalysis. As the name implies, phase transfer catalysis is carried out in a two-phase system; one phase is aqueous and the other is organic. In the alternative, a single anhydrous organic phase may contain a solid base, such as KOH, and either a quaternary amine or polyamine catalyst, such as tetramethylenediamine, in which the catalytic activity is at the surface of the base crystal. The catalyst utilized in the present invention is an alkylated quaternary amine, such as tetrabutylammonium sulfate, $C_8$-$C_{10}$ methyltrialkylammonium chloride, cetyltriethylammonium bromide, benzyltriphenylphosphonium chloride, hexadecyltrimethylammonium bromide, tetrapentylammonium bromide, and tetrahexylammonium chloride. The reactants are: $C_1$-$C_5$ alkyl halides; branched chain alkyl halides such as isopropyl bromide; aryl halides such as benzyl bromide; and acetylenic halides such as sa propargyl bromide. The general mechanism of synthesis by means of phase transfer-catalysis is as follows: first, the steroid anion complexes with the quaternary cation to form a lipophilic complex. The lipophilic complex is then transferred to the organic phase where it reacts with an alkyl halide to form an ether derivative of dexamethasone. The catalyst is then regenerated and passed back into the aqueous phase to react with the anion. The above-described method of synthesis is further illustrated by the examples set out below.

The above-described methods of synthesis are further illustrated by the examples set out below.

EXAMPLE 1

9α-fluoro-11β,17α-dihydroxy-21-methoxy-16α-methylpregna-1,4-diene-3,20-dione

To a 50 milliliter (ml) 3-necked round bottom flask fitted with a magnetic stirrer, heating mantle, addition funnel, and thermometer was added 15 ml of toluene, 3.25 grams (g) of Adogen 464 (methyltrialkyl ($C_8$-$C_{10}$) ammonium chloride) ($6.7 \times 10^{-3}$ moles (mol)) and 0.5 g of sodium chloride ($9 \times 10^{-3}$ mol). The stirred mixture was warmed to 35° C., at which time 2 g of dexamethasone ($5.1 \times 10^{-3}$ mol) was slowly added, followed by 5 ml of toluene. The mixture was stirred for 5 minutes, followed by the addition of 3 ml of 50% sodium hydroxide solution ($2.5 \times 10^{-2}$ mol). This mixture was equilibrated for 1-2 minutes, then 1.65 ml of iodomethane ($2.62 \times 10^{-2}$ mol, 5.1 equivalents) was added dropwise, which elevated the temperature to 37° C. Within 3 to 5 minutes following the addition of iodomethane, the yellow ether precipitated from the solution. The reaction was allowed to continue for an additional 20 minutes. At that time, the flask contents were poured into 200 ml of 5% sodium chloride solution in a separatory funnel, gently shaken, and the layers allowed to separate. The lower, highly alkaline, phase was drawn off and the organic phase was washed with well-mixed 20% volume/volume (v/v) toluene/water ($4 \times 200$ ml). The washed organic phase, left in the separatory funnel for 1 hour, underwent a secondary phase separation into clear yellow-brown upper layer (Adogen 464 catalyst) and a cloudy yellow lower layer. The lower layer was run into 250 ml of ice-cold ethyl ether which precipitated the white product. Precipitation of the product was completed by overnight a refrigeration at 4° C.

Residual Adogen catalyst was removed from the precipitated, filtered product with ether/toluene (200 ml) followed by ethyl ether (200 ml) and dried at 60° C. The product was further purified by silica-gel chromatography using ethyl acetate:hexane (1:1) as the eluant. M.P.=240°-241° C. (decomposition), $[\alpha]_D = 68.3°$ (1% dimethylformamide).

Calculated for $C_{23}H_{31}FO_5$: C=67.96%, H=7.70%. Found: C=67.8%, H=7.71%; CI/MS, M/z=406.

$^1$H NMR (DMSO-d$_6$): δ 0.76 (d, J=7, 3H) (C16 αCH$_3$); 0.85 (s, 3H) (C18-CH$_3$); 1.45 (s, 3H) (C19-CH$_3$); 3.24 (s,3H) (OCH$_3$); 4.15 (br. s, 1H) (C11 αH); 4.26(AB, J=18.4, Δν84, 2H) (C21-CH$_2$); 4.99 (s, 1H) (C17 αOH); 5.25 (br. s, 1H) (C11 βOH); 5.99 (s, 1H) (H-4); 6.20 (dd, J=10.1, J=1.9, 1H) (H-2); 7.27 (d, J=10.2, 1H) (H-1). (All coupling constants for all examples are reported in Hz.)

EXAMPLE 2

9αfluoro-11β,17αdihydroxy-21-benzyloxy-16α-methylpregna-1,4-diene-3,20-dione

In a manner similar to that of Example 1, 1.298 g of Adogen 464 ($2.67 \times 10^{-3}$ mol), 5 ml of toluene, 0.6 ml of a 50% sodium hydroxide solution ($5.2 \times 10^{-3}$ mol), and 9.5 ml of water was added to a 50 ml 3-necked round bottom flask. The rapidly stirred mixture was warmed to 24° C., at which time 2.0 g of dexamethasone ($5.1 \times 10^{-9}$ mol) was added slowly and the mixture allowed to equilibrate for 10 minutes. Benzyl bromide, 4.362 g ($2.55 \times 10^{-2}$ mol), was added dropwise over a period of 73 seconds. After 2 hours, the mixture was poured into 50 ml of ice-cold ethyl ether and the yellow precipitated product stirred for 15 minutes to remove the catalyst from the precipitate. The filtered precipitate was washed with ice-cold ether ($4 \times 100$ ml) followed by with ice-cold absolute ethanol ($4 \times 50$ ml) to afford pure white crystals of the product. The product was dried overnight at 60° C. Crystallization was from absolute ethanol. M.P.=243°-245° C. (decomposition).

Calculated for $C_{29}H_{35}FO_5$: C=72.19%, H=7.33%. Found: C=72.19%, H=7.34%; CI/MS, M/z=482.

$^1$H NMR (DMSO-d$_6$): δ 0.789 (d, J=7.1, 3H) (C16 αCH$_3$); 0.898 (s, 3H) a (C18-CH$_3$); 1.48 (s, 3H) (C19 CH$_3$); 4.29 (br. s, 1H) (C11 αH); 4.59 (AB, J=18.5, Δν=75.2, 2H) (C21-CH$_2$-O-); 4.68 (d, J=3.0, 2H) (C21—O—CH$_2$—); 5.02 (s, 1H) (C17 αOH); 5.27 (br. s, 1H) (C11 βOH); 6.00 (s, 1H) (H-4); 6.22 (dd, J=10.1, J=1.8, 1H) (H-2); 7.29 (d, J=10, 1H) (H-1); 7.35 (m, 5H) (C21—O—C—Ph).

EXAMPLE 3

9α-fluoro-11β,17α-dihydroxy-21-(2-methoxyethoxy)-methoxy-16α-methylpregna-1,4-diene-3,20-dione Dexamethasone, 1.6 g ($4.1 \times 10^{-3}$ mol), was combined with 35 ml of methylene chloride, 1.07 ml (1.5 equivalents) of N,N'-diisopropylethylamine (NDEA) and 0.7 ml ($6.13 \times 10^{-3}$ mol, 1.5 equivalents) of 2-methoxyethoxymethylchloride (MEMCL) in a 50 ml flask under rapid magnetic stirring at ambient temperature. This mixture remained as a suspension. After 1.5 hours, an additional equivalent each of MEMCL and NDEA were added and the reaction allowed to proceed for an additional 3.75 hours, after which time a solution was obtained. The flask contents were then washed with 100 ml of 5% HCl in a separatory funnel.

The lower organic phase was then removed and washed with water (4×100 ml). The organic phase was dried with MgSO$_4$, then combined, heated to the boiling point with 3 g of a celite:activated carbon mixture (1:1), cooled, and filtered. The clarified organic phase was evaporated to dryness and recrystallized from ethyl acetate. M.P.=193°-195° C. (decomposition).

Calculated for C$_{26}$H$_{37}$FO$_7$: C=64.98% H=7.78%. Found: C=65.25%, H=8.06%; CI/MS, M/z=480.

$^1$H NMR (DMSO-d$_6$): δ 0.718 (d, J=7.1, 3H) (C16 αCH$_3$); 0.866 (s, 3H) (C18-CH$_3$); 1.46 (s, 3H) (C19-CH$_3$); 3.25 (s, 3H) (OCH$_3$); 3.52 (dt, J=4.8, 4H) (C21 —O—(CH$_2$)$_2$—O); 4.42 (AB, J=18.4, Δν=74.5, 2H) (C21 —CH$_2$—O—); 4.66 (s, 2H) (C21 —O—CH$_2$—O ); 5.04 (s, 1H) (C17 αOH); 5.33 (br. d, J=4, 1H) (C11 βOH); 6.00 (s, 1H) (H-4); 6.22 (dd, J=10.1, J=1.8, 1H) (H-2); 7.29 (d, J=10, 1H) (H-1).

EXAMPLE 4

9α-fluoro-11β,17α-dihydroxy-21-(2-hydroxylethoxy-16α-methylpregna-1,4-diene-3,20-dione To a 50 ml 3-necked round bottom flask, fitted with a magnetic stirrer and a nitrogen source was added 10 ml of dry dimethylformamide (DMF), 2.83 g (1.88×10$^{-2}$ mol, 1.25 equivalents) of t-butyldimethylsilylchloride (TBDMS) and 3 g of imidazole (4.4×10$^{-2}$ mol) and stirred until all reagents were solubilized. 2-Bromoethanol, 1.87 g (1.5×10$^{-2}$ mol), was added dropwise and the reaction allowed to proceed for 4.25 hours at ambient temperature. The reaction mixture was combined with 400 ml of ether and 150 ml of water and then washed with water (4×200 ml). The organic phase was dried with MgSO$_4$ and evaporated down to a clear, off-white oil. Residual solvent was removed under high vacuum overnight. The reaction product, 2-bromoethanol silyl ether 1 was used without further purification in the subsequent alkylation reaction.

In a 50 ml 3-necked round bottom flask fitted with a magnetic stirrer, heating mantle, and a nitrogen source, 0.5 g of dexamethasone (1.28×10$^{-3}$ mol), and 0.8 g of 1 (3.35×10$^{-3}$ mol, 2.62 equivalents) were dissolved in 3 ml of hexamethyl-phosphoramide at 30° C. The reaction was started by the addition of 0.22 g (80%) of solid potassium hydroxide (3.14×10$^{-3}$ mol) and allowed to proceed for 70 minutes. An additional 1.64 equivalents of 1 was then added and the reaction allowed to proceed for an additional 60 minutes with the heat off. Under these conditions, the mono- and the bi-alkylated products formed with little or no degradation of the starting substrate. The reaction did not go to completion. The mono-alkylated steroid product 2 was partitioned between ethyl acetate/water (50 ml/25 ml) and the organic phase washed with water (4×50 ml). The product 2 was purified by silica gel chromatography using ethyl acetate:hexane (55:45) as the eluant. CI/MS gave the anticipated M/z=550 molecular ion and the correct H-NMR assignments for C21 "O" alkylation.

Silyl deprotection of 2 was carried out in a 50 ml 3-necked round bottom flask containing 0.080 g of 2 (1.45×10$^{-4}$ mol) and 0.155 g of tetrabutylammonium fluoride (5×10$^{-5}$ mol, 3 equivalents) in 2 ml of dry tetrahydrofuran for 20 minutes at ambient temperature. The deprotected, alkylated steroid 3 was partitioned into ethyl acetate/water (25 ml/15 ml) and the organic phase washed with water (4×15 ml), dried with MgSO$_4$, and evaporated to dryness. Crystallization was from acetone:hexane. M.P.=228°-230°.

Calculated for C$_{24}$H$_{33}$FO$_6$: C=66.05%, H=7.56%. Found: C=65.92%, H=7.94%; CI/MS, M/z=436.

$^1$H NMR (DMSO-d$_6$): δ 0.768 (d, J=7.1, 3H) (C16 αCH$_3$); 0.863 (s, 3H) (C18-CH$_3$); 1.47 (s, 3H) (C19-CH$_3$); 3.43 (m, 4H) (C21 —O—(CH$_2$)$_2$—O); 4.14 (br. s, 1H) (C11 αH); 4.36 (AB, J=18.6, Δν=82.7, 2H) (C21 —CH$_{13}$O); 4.6 (dd, J=4.7, 1H) (C21 13 O—C—OH); 4.99 (s, 1H) (C17 αOH); 5.27 (br. s, 1H) (C11 βOH); 5.99 (s, 1H) (H-4); 6.21 (dd, J=10, J=2, 1H) (H-2); 7.28 (d, J=10.3, 1H) (H-1).

EXAMPLE 5

9α-fluoro-11β,17α-methyl-dihydroxy-21-(methylthiolmethoxy)-16α-methylpregna-1,4-diene-3,20-dione Dexamethasone, 2 g (5.1×10$^{-3}$ mol), was added to a solution of 16.4 ml of dimethylsulfoxide (0.230 mol), 10.6 ml of acetic anhydride (0.1122 mol), and 3.2 ml of acetic acid (0.0561 mol) in a 100 ml 3-necked round bottom flask equipped with a magnetic stirrer and allowed to react for 24 hours at ambient temperature. The mixture was then neutralized by very slowly pouring the contents of the flask into 150 ml of 10% sodium carbonate solution and then adding 300 ml of ethyl acetate. The organic phase was washed successively with ethyl acetate saturated water (4×300 ml) and brine, and dried with MgSO$_4$. The evaporated organic base was purified by silica-gel chromatography using ethyl acetate:hexane (1:1) as the eluant. The product was crystallized from 30% ethanol. M.P.=221°-222° C. (decomposition).

Calculated for C$_{24}$H$_{33}$FO$_5$S: C=63.72%, H=7.30%. Found: C=63.71%, H=7.36%; CI/MS, M/z=452.

$^1$H NMR (DMSO-d$_6$): δ 0.784 (d, J=7.1, 3H) (C16 αCH$_3$); 0.865 (s, 3H) (C18-CH$_3$); 1.42 (s, 3H) (C19-CH$_3$); 2.09 (s, 3H) (C21 —S—CH$_3$); 4.16 (br. d, 1H) (C11 αH); 4.46 (AB, J=16, Δν=76.4, 2H) (C21 CH$_2$); 4.67 (s, 2H) (—O—CH$_2$S); 5.07 (s, 1H) (C17 OH); 6.0 (s, 1H) (H-4); 6.24 (dd, J=10.1, J=1.7, 1H) (H-2); 7.22 (d, J=10.2, 1H) (H-1).

EXAMPLE 6

9α-fluoro-11β,17α-dihydroxy-21-(methoxy)methoxy-16α-methylpregna-1,4-diene-3,20-dione Dexamethasone, 2 g (5.1×10$^{-3}$ mol), was dissolved in a solution of 10 ml of dry dimethylsulfoxide and 1.8 ml (2 equivalents) of N,N-diisopropylethylamine in a 50 ml 3-necked round bottom flask equipped with a magnetic stirrer under nitrogen. Chloromethoxymethyl ether, 0.775 ml (1.02×10$^{-2}$ mol, 2 equivalents), in a 1 ml Hamilton syringe, was added below the surface of the solution over a period of 1 minute, during which time the temperature rose from 23° to 29° C. The reaction proceeded over 105 minutes, a after which time an additional equivalent of chloromethoxymethyl ether was added. The reaction was continued for 18 hours, then partitioned into ethyl acetate/water 400 ml/200 ml), and the organic phase washed with water (2×200 ml), 200 ml of 1% sodium hydroxide solution, water (4×200 ml), and brine. The organic phase was dried with MgSO$_4$ and evaporated to dryness. The product was separated and purified by silica gel chromatography using ethyl acetate:hexane (65:35) as the eluant. Crystallization was from acetone:hexane. M.P.=243°-244° C. (decomposition).

Calculated for C$_{24}$H$_{33}$FO$_6$: C=66.06%, H=7.50%. Found: C=65.71%, H=7.57%; CI/MS, M/z=436.

¹H NMR (DMSO-d₆): δ 0.825 (d, J=13.2, 3H) (C16 αCH₃); 0.866 (s, 3H) (C18-CH₃); 1.46 (s, 3H) (C19-CH₃); 3.27 (s, 3H) (C21 —O—CH₃); 4.13 (br. s, 1H) (C11 αH); 4.41 (AB, J=18.4, Δν=73.5, 2H) (C21 CH₂); 4.57 (s, 2H) (C21 13 O—CH₂—O); 5.04 (s, 1H) (C17 αOH); 5.34 (s, 1H) (C11 βOH); 6.0 (s, 1H) (H-4); 6.25 (dd, J=10.1, J=2, 1H) (H-2); 7.32 (d, J=10.0, 1H) (H-1).

EXAMPLE 7

9α-fluoro-11β,17α-dihydroxy-Δ²⁰-ethoxy-21-ethoxy-16α-methylpregna-1,4-diene-3,20dione Potassium hydroxide was powdered in a hot mortar (75° C.) and 0.912 g (87.8%, $1.6 \times 10^{-2}$ mol) was added to 10 ml of dry dimethyl sulfoxide in a 50 ml 3-necked round bottom flask equipped with a magnetic stirrer and attached to a nitrogen source. After a 5 minute equilibration, 2 g of dexamethasone ($5.1 \times 10^{-3}$ mol) was added and, after dissolution, 2.4 g of iodomethane ($1.52 \times 10^{-2}$ mol, 3 equivalents) was added dropwise and the reaction allowed to proceed for 20 minutes at ambient temperature. The reaction was partitioned into ethyl acetate/water(100 ml/50 ml) and the organic phase washed with ethyl acetate saturated water (2×50 ml) and brine. The organic phase was dried with MgSO₄, evaporated to dryness, separated, and partially purified by silica gel chromatography using ethyl acetate:hexane (1:1) as the eluant. The analytical sample was crystallized repeatedly from acetone:hexane. M.P.=176°-177° C. (decomposition).

Calculated for C₂₆H₃₇FO₅: C=69.64%, H=8.25%. Found: C=69.73%, H=8.31%; CI/MS, M/z=448.

¹H NMR (DMSO-d₆): δ 0.865 (d, J=7.1, 3H) (C16 αCH₃); 0.942 (s, 3H) (C18-CH₃); 1.49 (s, 3H) (C19-CH₃); 1.56 (t, 3H) (C21 —O—C—CH₃); 1.76 (t, 3H) (C20 —O—C—CH₃); 3.69 (s, 1H) (C17αOH); 3.71 (q, 2H) (C21 O—CH₂—C); 3.92 (q, 2H) (C20 —O—CH₂—C); 4.09 (br.d, J=14, 1H) (11αH); 5.16 (s, 1H) (C11 βOH); 5.75 (s, 1H) (C21 enol H); 6.00 (s, 1H) (H-4); 6.21 (dd, J=10, J=1.7, 1H) (H-2); 7.22 (s, J=10.2, 1H) (H-1).

EXAMPLE 8

9α-fluoro-11β,17α-dihydroxy-21-ethoxy-16α-methylpregna-1,4-diene-3,20-dione

Sodium hydride (60% dispersion), 0.061 g ($2.55 \times 10^{-3}$ mol), was added to 10 ml of benzene in a 250 ml 3-necked round bottom flask fitted with a magnetic stirrer, nitrogen source, reflux condenser, and a dropping funnel. One g of dexamethasone ($2.55 \times 10^{-3}$ mol) dissolved in 50 ml of dry DMF was added dropwise over a period of 20 minutes, after which time the color changed from a light yellow to a dark yellow. Evolution of hydrogen gas, chased continuously by nitrogen, ceased at this point. At the cessation of hydrogen gas evolution, 3 equivalents of iodomethane ($7.7 \times 10^{-3}$ mol) was added to the rapidly stirred solution and the reaction allowed to proceed for 30 minutes at ambient temperature. The reaction products were partitioned into ethyl acetate:water (500 ml/500 ml) and the organic layer washed with water (3×100 ml) and brine. The organic phase was dried with sodium sulfate and evaporated down to a clear yellow oil. The oil was dissolved in ethyl acetate:hexane (1:1) and the product separated by silicagel chromatography. The product was crystallized from acetone:hexane. M.P.=239°-241° C. (decomposition). Calculated for C₂₄H₃₃FO₅: C=68.55%, H=7.93%. Found: C=68.59%, H=7.99%; CI/MS, M/z=420.

¹H NMR (DMSO-d₆): δ 0.775 (d, J=8.4, 3H) (C16 αCH₃); 0.864 (s, 3H) (CIB-CH₃); 1.48 (s, 3H) (C19-CH₃); 1.12 (t, J=6.9, 2H) (C21 —O—C—CH₃); 3.39 (q, J=5.6, 2H) (C21 —O—CH₂—C); 4.11 (br. s, 1H) (C11 αH); 4.32 (AB, J=18.5, Δν=81.5, 2H); (C21 CH₂); 5.00 (s, 1H) (17 αOH); 5.28 (s, 1H) (11 βOH); 6.00 (s, 1H) (H-4); 6.22 (dd, J=10.2, J=1.8, 1H) (H-2); 7.29 (d, J=10.1, 1H) (H-1).

EXAMPLE 9

9α-fluoro-11β,17α-dihydroxy-21-allyloxy-16α methylpregna-1,4-diene-3,20-dione

Powdered potassium hydroxide (87.7%), 0.456 g ($8.14 \times 10^{-3}$ mol), was added to 10 ml of dry dimethylsulfoxide in a 50 ml 3-necked round bottom flask fitted with a magnetic stirrer and a nitrogen source. After the contents were stirred for 5 minutes, 1 g of dexamethasone ($2.55 \times 10^{-3}$ mol) was added slowly until dissolved. Allylbromide, 0.32 g ($2.64 \times 10^{-3}$ mol, 1 equivalent) was added dropwise over 1 minute and the reaction allowed to proceed for 10 minutes. The reaction products (minus solid potassium hydroxide) were transferred with ethyl acetate and partitioned into ethyl acetate/water (100 ml/200 ml). The organic layer was washed with water (3×100 ml), brine (2×15 ml), dried with MgSO₄, and evaporated to dryness. The product was separated and purified by silica gel chromatography using ethyl acetate:hexane (1:1) as the eluant. The product was crystallized from acetone:hexane. M.P.=245.5°-248.5° C. (decomposition).

Calculated for C₂₅H₃₃FO₅: C=69.44%, H=7.64%. Found: C=69.59%, H=7.87%; CI/MS, M/z=432.

¹H NMR (DMSO-d₆): δ 0.779 (d, J=7.1, 3H) (C16 αCH₃);0.872 (s, 3H) (C18-CH₃); 1.49 (s, 3H) (C19-CH₃); 3.95 (q, 2H) (C21 —C—O—CH₂); 4.19 (br. s, 1H) (C11 αH); 4.55 (AB, J=18.5, Δν=85.2, 2H) (C21 CH₂); 5.00 (s, 1H) (C17 αOH); 5.23 (m, 2H) (C21—C=CH₂); 5.89 (m, 1H) (C21 —CH=C); 6.00 (s, 1H) (H-4); 6.22 (dd, J=10.1, J=1.8, 1H) (H-2); 7.27 (d, J=10.1, 1H) (H-1).

EXAMPLE 10

9α-fluoro-11β,17α-dihydroxy-21-cyclopropylmethoxy-16α-methylpregna-1,4-diene-3,20-dione Powdered potassium hydroxide (87.7%), 0.456 g ($8.14 \times 10^{-3}$ mol), was added to 10 ml of dry dimethylsulfoxide in a 50 ml 3-necked round bottom flask fitted with a magnetic stirrer and a nitrogen source. After the flask contents were stirred for 10 minutes, 1 g of dexamethasone ($2.55 \times 10^{-3}$ mol) was added slowly until dissolved. Cyclopropylmethylbromide, 0.342 g ($2.58 \times 10^{-10}$ mol, 1 equivalent), was added dropwise over 1 minute and the reaction allowed to proceed for 15 minutes at ambient temperature. The reaction products (minus solid potassium hydroxide) were transferred with ethyl acetate and partitioned into ethyl acetate/water (100 ml/200 ml). The organic phase was washed with water (3×200 ml), brine (2×15 ml), dried with MgSO₄, and evaporated to dryness. The product was separated and purified by silica gel chromatography using ethyl acetate:hexane (7:3) as the eluant. M.P.=238.5°-239.5° C. (decomposition).

Calculated for C₂₆H₃₅FO₅: C=69.96%, H=7.85%. Found: C=69.78%, H=7.99%; CI/MS, M/z=446.

¹H NMR (DMSO-d₆): δ 0.323 (m, 5H) (C21 —C—CH—cy(C₃H₅)); 0.775 (s, 3H) (C16αCH₃); 0.863 (s, 1H)

(C18-CH$_3$); 1.49 (s, 3H) (C19-CH$_3$); 3.23 (dd, J=2.3, J=6.8, 2H) (C21 —O—CH$_2$—cyc(C$_3$H$_5$)); 4.11 (br. d, J=8.3, 1H) (C11 αH); 4.34 (AB, J=18.5, Δν=82.2, 2H) (C21 CH$_2$—O—); 4.98 (s, 1H) (C17 αOH); 5.27 (s 1H) (C11 βOH); 6.00 (s, 1H) (H-4); 6.22 (dd, J=10.1, J=1.87, 1H) (H-2); 7.29 (d, J=10.2, 1H) (H-1).

EXAMPLE 11

9α-fluoro-11β,17α-dihydroxy-21-allyl-21-allyloxy-16α-methyl-1,4-diene-3,20-dione In a manner similar to that of Example 1, 14 ml of toluene and 1.68 g of Adogen 464 (3.42×10$^{-3}$ mol) was added to a 50 ml 3-necked round bottom flask and warmed to 32° C. At this temperature, 1.5 g of 50% sodium hydroxide solution (3.75×10$^2$ mol) was added and the flask contents equilibrated for 5 minutes. Dexamethasone, 1 g (2.55×10$^{-3}$ mol), was added slowly until dissolved and equilibrated for 3 minutes. Allylbromide, 0.924 g (7.6×10$^{-3}$ mol, 3 equivalents), was added dropwise over 1 minute and the reaction allowed to proceed for 20 minutes at 32° C. The reaction contents were partitioned into 300 ml of ethyl acetate/water 300 ml/400 ml). The organic phase was washed with water (2×400 ml), brine (2×15 ml), dried with MgSO$_4$, and evaporated down to a clear, slightly yellow, glass. The product was isolated by silica gel chromatography using ethyl acetate:hexane as the eluant. No M.P. - product amorphous.

Calculated for C$_{28}$H$_{37}$FO$_5$: C=71.19%, H=7.85%. Found: C=70.45%, H=7.83%; CI/MS, M/z=472.

$^1$H NMR (DMSO-d$_6$): δ 0.871 (d, J=7.1, 3H) (C16 αCH$_3$); 0.949 (s, 3H) (C18-CH$_3$); 1.49 (s, 3H) (C19-CH$_3$); 4.15 (br. d, 1H) (C11 αH); 4.2 (br. m, 5H) (C21 -allyl); 4.88 (s, 1H) (C17 OH); 5.14 (br. m, 5H) (C21 -allyl); 5.33 (br. s, 1H) (C11 βOH); 5.81 (m, 2H) (C21 -allyl); 6.01 (s, 1H) (H-4); 6.22 (dd, J=9.9, J=1.8, 1H) (H-2): 7.28 (d, J=10.1, 1H) (H-1).

EXAMPLE 12

9α-fluoro-11β,17α-hydroxy-21-isopropyloxy-16α-methylpregna-1,4-diene-3,20-dione

Powdered potassium hydroxide (87.7%), 0.456 g (8.14×10$^{-3}$ mol), was added to 7 ml of dry dimethylsulfoxide in a 50 ml 3-necked round bottom flask equipped with a magnetic stirrer and a nitrogen source. The reaction was allowed to equilibrate for 5 minutes, then 1 g of dexamethasone (2.55×10$^{-3}$ mol) was added slowly until dissolved. 2-Bromopropane, 0.914 g (7.65×10$^{-3}$ mol, 3 equivalents), was added dropwise over 1 minute and the reaction allowed to proceed for 15 minutes at ambient temperature. The reaction solution was partitioned into ethyl acetate/water (105 ml/75 ml) and the organic phase washed with ethyl acetate saturated water (3×50 ml) and brine (2×15 ml). The organic phase was dried with MgSO$_4$, evaporated to dryness, and partially a purified by silica gel chromatography using acetone:hexane (7:3) as the eluant. The product was crystallized repeatedly from acetone:ether. M.P.= 232°-233.5° C. (decomposition).

Calculated for C$_{25}$H$_{35}$FO$_5$: C=69.10%, H=8.12%. Found: C=69.02%, H=8.32%; CI/MS molecular ion, M/z=434.

$^1$H NMR (DMSO-d$_6$): δ 0.785 (d, J=7.2, 3H) (C16 αCH$_3$); 0.861 (s, 3H) (C18 CH$_3$); 1.07 (m, 6H) (C21 —O—C—(CH$_3$)$_2$); 1.48 (s, 3H) (C19 CH$_3$); 3.55 (m, 1H) (C21 —O—CH—(CH$_3$)$_2$); 4.11 (br. s, 1H) (C11-H); 4.32 (AB, J=18.5, Δν=81.5, 2H) (C21 CH$_2$—O—); 4.98 (s, 1H) (C17 αOH); 5.29 (br. t, 1H) (C11 βOH); 6.03 (s, 1H) (H-4); 6.22 (dd, J=10.1, J=1.8, 1H) (H-2); 7.28 (d, J=10.2, 1H) (H-1).

EXAMPLE 13

9α-fluoro-11β-propionoxy-17α-hydroxy-21-methoxy-16α-methylpregna-3,20-dione

The compound of Example 1, 0.8 g(1.97×10$^{-3}$ mol), was suspended in 5 ml of N,N-dimethylformamide and 25 ml of pyridine in a 250 ml 3-necked round bottom flask equipped with a magnetic stirrer and nitrogen source. Propionic anhydride, 0.76 ml (3 equivalents), and 0.040 g (0.016 equivalent) of 4-dimethylaminopyridine (DMAP) were added and the mixture stirred for 2 hours at ambient temperature. The substrate at this point remained in suspension. After 3 hours, an additional equivalent of DMAP (0.24 g) and 7 equivalents (1.8 ml) of propionic anhydride were added and the reaction allowed to proceed for 16 hours at ambient temperature. The clear, light yellow solution was equilibrated with 200 ml ethyl acetate and 100 ml of 4% HCl. The organic phase was washed sequentially with 80 ml of 5% HCl, 3×80 ml of 3% HCl, solution and 200 ml of water. The light brown organic phase was dried with brine and MgSO$_4$, followed by charcoal-celite in hot ethyl acetate, and evaporated down to a clear glass. Trituration with ethyl ether, ethyl ether/hexane gave a white powder which was twice crystallized from ethyl acetate/isopropyl ether to give very fine needles. NMR indicated that the product crystallized as an ethyl acetate solvate of approximately ½mol. M.P.=178-178.5; M/z=462.

Calculated for C$_{26}$H$_{35}$FO$_6$.½(C$_4$H$_8$O$_2$): C=66.38%, H=7.75%. Found C=66.74%, H=7.96%.

$^1$H NMR (DMSO-d$_6$): δ 0.79 (d, J=7.0, 3H) (C16 CH$_3$); 0.79 (s, 3H) (C18 CH$_3$); 1.4 (s, 3H) (C19 CH$_3$); 2.4 (q, J=7.5, 2H)(C11 βCOCH$_2$—C); 3.2 (s, 3H) (C21 —O—CH$_3$); 4.1 (t, J=7.5, 3H) (C11 βCO—C—CH$_3$); 4.26 (AB, J=18.4, Δν=81.0) (C21 CH$_2$); 5.17 (s, 1H) (C17 αOH); 5.22 (m, 1H) (C11 αH); 6.1 (s, 1H) (H4); 6.3(dd, J=1.8, J=−10.1, 1H) (H2); 6.8 (d, J=10.1, 1H) (H1).

EXAMPLE 14

9α-fluoro-11β-17α-diacetoxy-21-methoxy-16α-methyl-pregna-1,4-diene-3,20-dione

The compound of Example 1, 1.0 g (2.46×10$^{-3}$ mol), was combined with 5 ml of glacial acetic acid and 5 ml of acetic anhydride under nitrogen in a 50 ml, 3-necked round bottom flask equipped with a magnetic stirrer in an 40° C. oil bath. When the temperature reached 79°-81° C., 0.233 g of p-toluenesulfonic acid monohydrate (0.5 equivalent) was added and the reaction allowed to proceed for 5.5 hours. The reaction contents were suspended in ethyl acetate/water (200 ml/200 ml) and the organic phase washed with water (6×200 ml) to neutrality. The organic phase was dried with MgSO$_4$ and by-products removed with charcoal-celite in hot ethyl acetate. The product was isolated on 200 g of silica gel using ethyl acetate:toluene (4:7) as the eluant. M.P. 120° C.-123° C.; M/z=490.

Calculated for C$_{27}$H$_{35}$FO$_7$; C=66.10%; H=7.19%. Found C=66.24%, H=7.61%.

$^1$H NMR (DMSO-d$_6$): δ 0.85 (s, 3H) (C18 CH$_3$); 0.86 (d, J=6.7, 3H) C16 αCH$_3$); 1.37 (s, 3h) (C19 CH$_3$); 4.1 (s, 2H) (COCH$_2$—O); 5.2 (m, 1H) (C11 αH); 6.1 (s, 1H)

(H4); 6.3 (dd, J−1.8, J=10.1, 1H) (H2); 6.82 (d, J=10.1, 1H) (H1).

The steroid derivatives of Formula (I) and (II) may be incorporated into various types of ophthalmic pharmaceutical compositions for delivery to the eye. For example, one or more of these compound may be combined with ophthalmologically acceptable preservatives, surfactants, viscosity enhancers, buffers, sodium chloride and water to form an aqueous, sterile ophthalmic suspension.

In order to prepare sterile ophthalmic ointment formulations, one or more of the compound is combined with a preservative in a hydrophilic/hydrophobic base such as mineral oil, liquid lanolin, or white petrolatum. Sterile ophthalmic gel formulations may be prepared by suspending the active ingredient in a hydrophilic base prepared from the combination of Carbopol-940 (a carboxy vinyl polymer available from the B. F. Goodrich Company), sodium hydroxide, sodium chloride, and preservatives. The specific type of formulation selected will depend on various factors, such as the type of inflammation being treated (e.g., internal or external) and dosage frequency. Ophthalmic suspensions, ointments, and gels are the preferred dosage forms.

In addition, the formulations will normally include conventional ingredients such as preservatives, tonicity agents, and so on. The steroid derivatives of Formula (I) and (II) will normally be contained in these formulations in an amount in the range of 0.05% to 2.0% by weight.

The formulations described in the following example further illustrate the dosage forms which may be utilized in the present invention.

EXAMPLE 15

In the following formulations, the term "steroid" represents any of the above-described C21 steroid derivatives of Formula (I) and (II), including the following specific example of such derivatives: 9α-fluoro-11β,17α-dihydroxy-21-methoxy-16α-methylpregna-1,4-diene-3,20dione.

| Ingredient | Percentage by weight |
|---|---|
| Suspension | |
| Steroid | .05–2.0 |
| Benzalkonium Chloride | 0.001–0.02 |
| Polysorbate-80 or Tyloxopol | 0.01–1.0 |
| Phosphate Buffer pH | 5–100 mMol |
| Sodium Chloride | 0–0.9 |
| Hydroxypropyl methyl cellulose | 0.1–0.5 |
| Water | q.s. |
| Ointment | |
| Steroid | 0.05–2.0 |
| Chlorobutanol | 0.5 |
| Methyl or propyl parabens | 0.01–0.1 |
| Mineral Oil | 0–10 |
| Liquid Lanolin | 0–10 |
| White petrolatum | q.s. |
| Gel | |
| Steroid | 0.05–2.0 |
| Carbopol-940 | 1–4 |
| Sodium Hydroxide (q.s.) pH: | 4.5–8.0) |
| Sodium Chloride | 0–0.9 |
| Water | q.s. |

The treatment method of the present invention comprises applying an a ophthalmic pharmaceutical composition containing an anti-inflammatory effective amount of one or more steroid derivatives of Formula (I) or (II) to the affected ocular tissue when indicated for the relief of inflammation.

Examples of ophthalmic inflammatory disorders which can be treated by the compositions of the present invention include, but are not limited to: acute or chronic conjunctivitis; acute or chronic anterior segmental uveitis in normal individuals, steroid responders, and individuals with frank primary open and/or closed angle glaucoma; inflammation and IOP elevation resulting from intraocular lens implantation and/or inflammation; and IOP elevation following trabecular filtering or laser surgeries. The dosage regimen utilized will depend on various factors, such as the severity of the inflammation and the duration of action of the particular formulation utilized. In general, the above-described formulations may be topically applied, for example, as drops to the upper globe, or as a 0.5–1.0 cm strip of ointment or gel to the lower conjunctival sac of the eye. Suspensions will generally be applied two to four times daily, while ointments or gels will generally be applied once or twice daily. The application of sustained release formulations (e.g., polymer based gels) once daily at bedtime will be preferred for some conditions.

The above-described formulations are useful in treating virtually any a type of ocular inflammation. These formulations are especially useful in the treatment of ocular inflammation in patients who are predisposed to experiencing elevated intraocular pressure when treated with a conventional steroid compound; this class of patients, which is estimated as constituting approximately 5% of the general population, is referred to as "steroid responders." The formulations also have special value in treating ocular inflammation in patients suffering from open angle glaucoma, sinceit has been estimated that approximately 92% of these patients experience a large increase in intraocular pressure after chronic (e.g., 6 to 8 weeks) steroid therapy. The formulations also find special use in treating the inflamed ocular tissue of patients who are predisposed to open-angleglaucoma or ocular hypertension.

The present invention has been described above in connection with certain preferred embodiments. However, as obvious variations thereon will become apparent to those skilled in the art, the invention is not to be considered as limited thereto.

What is claimed is:

1. A method of treating inflamed ocular tissue which comprises topically applying to an affected eye an anti-inflammatory effective amount of a compound of formula:

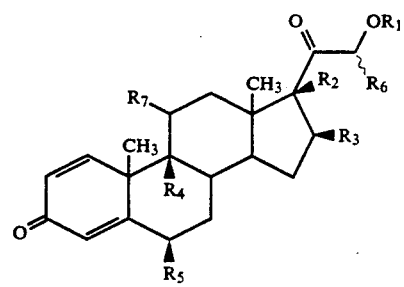

wherein:
$R_1$ is selected from substituted or unsubstituted: $C_1$–$C_5$ alkyl; $C_3$–$C_6$ (ring) and $C_1$–$C_3$ (alkyl) cycloalkyl and cycloalkylalkyl; aryl and arylalkyl, such as phenyl and benzyl; and $C_2$-$C_5$ alkenyl and alkynyl; wherein the substituent or substituents are selected from $C_1$-$C_6$ alkyoxy and alkyl; $C_2$-$C_6$ alkoxyalkyl, alkoxyalkoxyalkyl, alkylthioalkyl, hydroxyalkyl, aminoalkyl, nitriloalkyl; $C_4$-$C_8$ (beta-carboxyalkoxy)alkyl; and $C_2$-$C_6$ alkenoxy and alkynoxy;

$R_2$ is selected from substituted or unsubstituted: $C_1$-$C_6$alkyl, alkenyl and alkynyl; acyl; and hydroxyl; wherein the substituent or substituents are selected from: $C_1$-$C_3$ alkyl; hydroxyl; and halogen (F,Cl, and Br);

$R_3$ is selected from methyl and hydroxyl;

$R_4$ is selected from hydrogen, fluoro, and chloro;

$R_5$ is selected from hydrogen, methyl, fluoro, and chloro;

$R_6$ is selected from hydrogen, methyl, ethyl, and allyl; and $R_7$ is selected from hydroxyl, acetate, propionate, and butyrate;

or a pharmaceutically acceptable salt thereof; wherein the topical application of said compound does not significantly increase the intraocular pressure of the affected eye.

2. A method of treating inflamed ocular tissue according to claim 1, wherein:

R is selected from methyl, ethyl, propyl, butyl, allyl, cyclopropyl, cyclobutyl, cyclopentyl, cyclohexyl, phenyl, benzyl, isopropyl, isobutyl, isoamyl, isovaleryl, 2-propynyl, and 2-methoxymethyl methylthiomethyl, hydroxyethyl, and methoxy ethoxymethyl;

$R_2$ is selected from hydrogen, methyl, ethyl, propyl, butyl, amyl, acetate, propionate, butyrate, valerate, 2-propynyl, and hydroxyl;

$R_3$ is selected from methyl and hydroxyl;

$R_4$ is selected from hydrogen, fluoro and chloro;

$R_5$ is selected from hydrogen, methyl, fluoro and chloro;

$R_6$ is selected from hydrogen, methyl, ethyl, and ally; and $R_7$ is hydroxyl.

3. A method of treating inflamed ocular tissue according to claim 2, wherein $R_2$, $R_3$ and $R_4$ are, respectively, hydroxyl, methyl and fluoro.

4. A method of treating inflamed ocular tissue according to claim 1, wherein $R_5$ is methyl.

5. A method of treating inflamed ocular tissue according to claim 2, wherein $R_5$ is methyl.

6. A method of treating inflamed ocular tissue according to claim 3, wherein $R_5$ is methyl.

7. A method of treating inflamed ocular tissue according to claim 3, wherein $R_5$ is hydrogen.

8. A method of treating inflamed ocular tissue according to claim 2, wherein $R_2$ and $R_3$ are hydroxyl and $R_4$ and $R_5$ are fluoro.

9. A method of treating inflamed ocular tissue according to claim 1, wherein $R_2$ is selected from hydrogen, acetate, propionate, butyrate, valerate and 2-propynyl.

10. A method of treating inflamed ocular tissue according to claim 9, wherein $R_3$ is hydroxyl and $R_4$ and $R_5$ are fluoro.

11. A method of treating inflamed ocular tissue according to claim 1, wherein $R_1$ is methyl, $R_2$ is hydroxyl, $R_3$ is methyl, $R_4$ is fluoro and $R_5$ is hydrogen.

12. A method of treating inflamed ocular tissue which comprises topically applying to an affected eye an anti-inflammatory effective amount of a compound of formula:

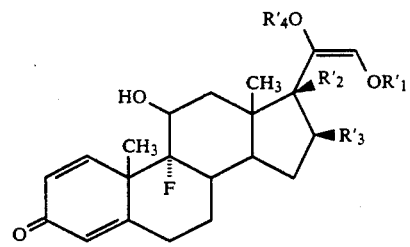

wherein:

$R'_1$ is selected from substituted or unsubstituted: $C_1$-$C_5$ alkyl, alkenyl, and alkynyl;

$R'_2$ is selected from substituted or unsubstituted: hydrogen; $C_1$-$C_6$ alkyl, alkenyl, alkynyl; acyl; and hydroxyl; wherein the substituent or substituents are selected from: $C_1$-$C_3$ alkyl; hydroxyl; and halogen;

$R'_3$ is selected from methyl and hydroxyl; and $R'_4$ is selected from $C_1$-$C_5$ alkyl, alkenyl, and alkynyl;

wherein the topical application of said compound does not significantly increase the intraocular pressure of the affected eye.

13. A method of treating inflamed ocular tissue according to claim 12 wherein:

$R'_1$ is selected from the methyl, ethyl, and allyl;

$R'_2$ is selected from hydroxyl, acetate, and propionate;

$R'_3$ is selected from methyl and hydroxyl; and $R'_4$ is selected from methyl, ethyl, and allyl.

14. A method of treating inflamed ocular tissue according to claim 13 wherein:

$R'_1$ is selected from methyl, ethyl, and ally;

$R'_2$ is selected from hydroxyl, acetate, and propionate; and $R'_3$ is methyl.

15. A pharmaceutical composition for treating ophthalmic inflammation, comprising an anti-inflammatory effective amount of a compound of formula:

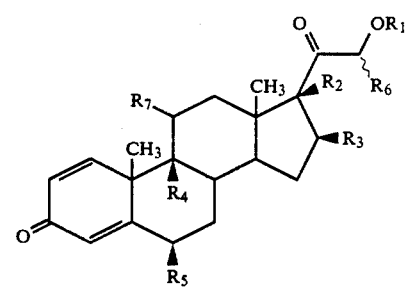

wherein:

$R_1$ is selected from substituted or unsubstituted: $C_1$-$C_5$ alkyl; $C_3$-$C_6$ (ring) and $C_1$-$C_3$ (alkyl) cycloalkyl and cycloalkylalkyl; aryl and arylalkyl, such as phenyl and benzyl; and $C_2$-$C_5$ alkenyl and alkynyl; wherein the substituent or substituents are selected from $C_1$-$C_6$ alkyoxy and alkyl; $C_2$-$C_6$ alkoxyalkyl, alkoxyalkoxyalkyl, alkylthioalkyl, hydroxyalkyl, aminoalkyl, nitriloalkyl; $C_4$-$C_8$ (beta-carboxyalkoxy)alkyl; and $C_2$-$C_6$ alkenoxy and alkynoxy;

$R_2$ is selected from substituted or unsubstituted: $C_1-C_6$ alkyl, alkenyl and alkynyl; acyl; and hydroxyl; wherein the substituent or substituents are selected from: $C_1-C_3$ alkyl; hydroxyl; and halogen (F,Cl, and Br);

$R_3$ is selected from methyl and hydroxyl;

$R_4$ is selected from hydrogen, fluoro, and chloro;

$R_5$ is selected from hydrogen, methyl, fluoro, and chloro;

$R_6$ is selected from hydrogen, methyl, ethyl, and allyl; and $R_7$ is selected from hydroxyl, acetate, propionate, and butyrate;

or a pharmaceutically acceptable salt thereof;

and a pharmaceutically acceptable vehicle therefor; wherein the topical application of said compound does not significantly increase the intraocular pressure of the affected eye.

16. A pharmaceutical composition for treating ophthalmic inflammation, comprising an anti-inflammatory effective amount of a compound of formula:

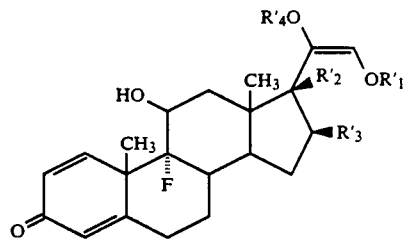

wherein:

$R'_1$ is selected from substituted or unsubstituted: $C_1-C_5$ alkyl, alkenyl, and alkynyl;

$R'_2$ is selected from substituted or unsubstituted: hydrogen; $C_1-C_6$ alkyl, alkenyl, alkynyl; acyl; and hydroxyl; wherein the substituent or substituents are selected from: $C_1-C_3$ alkyl; hydroxyl; and halogen;

$R'_3$ is selected from methyl and hydroxyl; and $R'_4$ is selected from $C_1-C_5$ alkyl, alkenyl, and alkynyl;

and a pharmaceutically acceptable vehicle therefor; wherein the topical application of said compound does not significantly increase the intraocular pressure of the affected eye.

* * * * *

UNITED STATES PATENT AND TRADEMARK OFFICE
CERTIFICATE OF CORRECTION

PATENT NO. : 5,223,493  Page 1 of 3
DATED : June 29, 1993
INVENTOR(S) : John J. Boltralik It is certified that error appears in the above-identified patent and that said Letters Patent is hereby corrected as shown below:

Column 4, structure 3 should read:

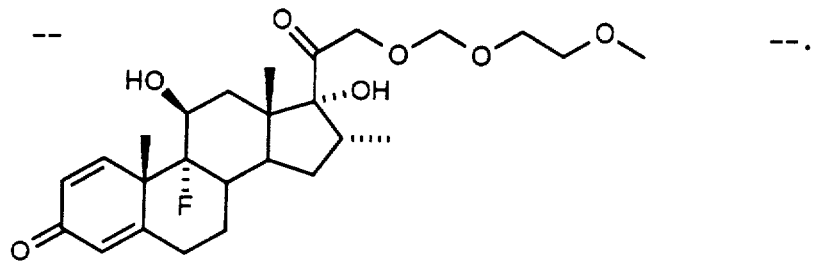

Column 16, the formula in claim 1 should read:

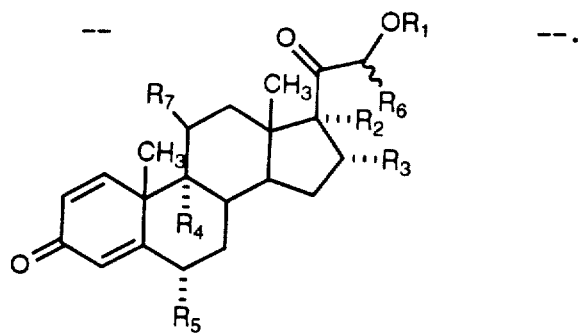

UNITED STATES PATENT AND TRADEMARK OFFICE
CERTIFICATE OF CORRECTION

PATENT NO. : 5,223,493

DATED : June 29, 1993

INVENTOR(S) : John J. Boltralik

It is certified that error appears in the above-identified patent and that said Letters Patent is hereby corrected as shown below:

Column 18, the formula in claim 12 should read:

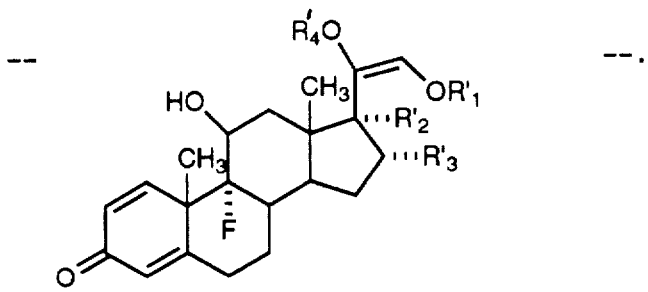

Column 18, the formula in claim 15 should read:

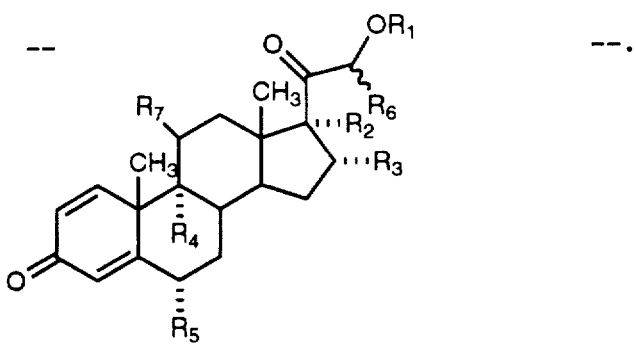

UNITED STATES PATENT AND TRADEMARK OFFICE
CERTIFICATE OF CORRECTION

PATENT NO. : 5,223,493

DATED : June 29, 1993

INVENTOR(S) : John J. Boltralik

Page 3 of 3

It is certified that error appears in the above-identified patent and that said Letters Patent is hereby corrected as shown below:

Column 20, the formula in claim 16 should read:

-- 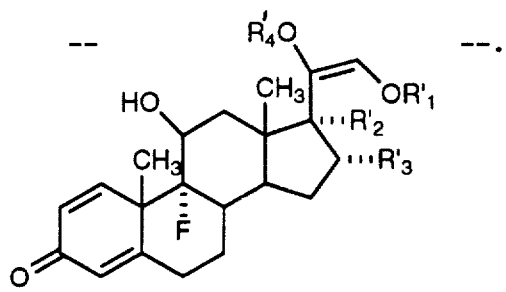 --.

Signed and Sealed this

Twenty-sixth Day of April, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,223,493

DATED : June 29, 1993

INVENTOR(S) : Boltralik

It is certified that error appears in the above-identified patent and that said Letters Patent is hereby corrected as shown below:

Col. 2, line 51: "cycloalkylalKyl" should read --cycloalkylalkyl--.

Col. 2, line 53, "from" should read --from:--.

Col. 2, line 54: "alkyoxy" should read --alkoxy--.

Col. 2, line 58: "from substituted" should read --from hydrogen and substituted--.

Col. 2, line 59: "acyl (-COOR;" should read --acyloxy (-OCOR;--.

Col. 3, lines 1-2: "acetate, propionate, and butyrate;" should read --acetyloxy, propanoyloxy, and butanoyloxy:--.

Col. 3, lines 18-19: "from substituted or unsubstituted: hydrogen;" should read --from hydrogen and substituted or unsubstituted:--.

Col. 3, line 19: "acyl" should read --acyloxy--.

Col. 3, line 34: "methoxyethylmethyl" should read --methoxyethoxymethyl--.

Col. 3, line 36: "acetate, propionate, butyrate, valerylate" should read --acetyloxy, propanoyloxy, butanoyloxy, valeroyloxy--.

Col. 3, line 37: "and a hydroxyl;" should read --and hydroxyl;--.

Col. 3, line 44: "acetate, and propionate" should read --acetyloxy and propanoyloxy--.

Col. 3, line 48: "acetate, and propionate" should read --acetyloxy and propanoyloxy--.

Col. 3, line 67: "carboalkyl" should read "acyloxy--.

UNITED STATES PATENT AND TRADEMARK OFFICE
CERTIFICATE OF CORRECTION

PATENT NO. : 5,223,493

DATED : June 29, 1993

INVENTOR(S) : Boltralik

It is certified that error appears in the above-identified patent and that said Letters Patent is hereby corrected as shown below:

Col. 3, lines 67-68: "acetate, propionate, butyrate, valerylate" should read
--acetyloxy, propanoyloxy, butanoyloxy, valeroyloxy--.

Col. 4, line 6: "acetate, and propionate" should read --acetyloxy, and propanoyloxy--.

Col. 7, line 22: "as sa propargyl" should read --as propargyl--.

Col. 17, line 3: "alkyoxy" should read --alkoxy--.

Col. 17, line 8: "from substituted" should read --from hydrogen and substituted"--.

Col. 17, line 9: "acyl" should read --acyloxy--.

Col. 17, lines 19-20: "acetate, propionate, and butyrate;" should read
--acetyloxy, propanoyloxy, and butanoyloxy;--.

Col. 17, line 30: "2-propynyl, and 2-methoxymethyl methyl-" should read
--2-propynyl, 2-methoxymethyl, methyl- --.

Col. 17, line 34: "acetate, propionate, butyrate, valerate," should read
--acetyloxy, propanoyloxy, butanoyloxy, valeroyloxy,--.

UNITED STATES PATENT AND TRADEMARK OFFICE
CERTIFICATE OF CORRECTION

PATENT NO. : 5,223,493

DATED : June 29, 1993

INVENTOR(S) : Boltralik

It is certified that error appears in the above-identified patent and that said Letters Patent is hereby corrected as shown below:

Col. 17, line 40: "ally;" should read --allyl;--.

Col. 17, line 59: "acetate, propionate, butyrate, valerate" should read
    --acetyloxy, propanoyloxy, butanoyloxy, valeroyloxy--.

Col. 18, lines 18-19: "from substituted or unsubstituted: hydrogen;" should read
    --from hydrogen and subsituted or unsubstituted:--.

Col. 18, line 19: "acyl" should read --acyloxy--.

Col. 18, lines 31-32: "acetate, and propionate;" should read --acetyloxy and propanoyloxy;--.

Col. 18, line 37: "ally;" should read --allyl;--.

Col. 18, lines 38-39: "acetate, and propio-nate;" should read --acetyloxy and propanoyloxy;--.

Col. 18, line 64: "from" should read --from:-- and "alkyoxy" should read --alkoxy--.

Col. 19, line 2: "$C_1$-$C_6$alkyl" should read --$C_1$-$C_6$ alkyl--.

Col. 19, line 2: "acyl" should read "acyloxy--.

Col. 19, lines 15-16: "acetate, propionate, and butyrate;" should read
    --acetyloxy, propanoyloxy, and butanoyloxy;--.

Col. 20, lines 15-16: "from substituted or unsubstituted: hydrogen;" should read
    --from hydrogen and substituted or unsubstituted:--.

UNITED STATES PATENT AND TRADEMARK OFFICE
CERTIFICATE OF CORRECTION

PATENT NO. : 5,223,493
DATED : June 29, 1993
INVENTOR(S) : Boltralik

It is certified that error appears in the above-indentified patent and that said Letters Patent is hereby corrected as shown below:

Col. 20, line 16: "acyl" should read --acyloxy--.

Signed and Sealed this

Second Day of January, 1996

Attest:

BRUCE LEHMAN

Attesting Officer     Commissioner of Patents and Trademarks